United States Patent
Kunde et al.

(12) 
(10) Patent No.: US 6,297,362 B1
(45) Date of Patent: Oct. 2, 2001

(54) AZO DYES

(75) Inventors: Klaus Kunde, Neunkirchen-Seelscheid; Michael-Thomas Jörss, Kerpen; Peter Wild, Odenthal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/411,165

(22) Filed: Oct. 1, 1999

(30) Foreign Application Priority Data

Oct. 5, 1998 (DE) .............................................. 198 45 640

(51) Int. Cl.$^7$ ........................... C09B 43/16; C09B 29/22; C09B 29/09; C09B 29/36; C09B 31/14; C09D 11/02; C09D 11/00

(52) U.S. Cl. .................................. 534/798; 8/662; 8/682; 8/688; 534/804; 534/849; 106/31.77; 106/31.8; 106/496

(58) Field of Search ..................................... 534/804, 798, 534/849; 8/688, 662; 106/31.77, 31.8, 496

(56) References Cited

U.S. PATENT DOCUMENTS

| | | | |
|---|---|---|---|
| 4,664,714 | * | 5/1987 | Katsura et al. ................... 106/308 N |
| 5,599,386 | | 2/1997 | Sano et al. ......................... 106/22 R |
| 5,684,140 | | 11/1997 | Baettig et al. ...................... 534/803 |
| 5,710,258 | * | 1/1998 | Adam et al. ........................ 534/643 |
| 5,721,344 | | 2/1998 | Baettig ............................... 534/776 |
| 5,859,216 | | 1/1999 | Adam et al. ......................... 534/776 |
| 5,929,215 | * | 7/1999 | Pedrazzi ............................. 534/604 |

FOREIGN PATENT DOCUMENTS

| | | | |
|---|---|---|---|
| 2547794 | * | 5/1976 | (DE) ................................... 534/798 |
| 065479 | | 5/1982 | (EP) . |
| 024668 | | 4/1983 | (EP) . |
| 755984 | | 1/1997 | (EP) . |
| 96/24636 | | 8/1996 | (WO) . |

* cited by examiner

Primary Examiner—Floyd D. Higel
(74) Attorney, Agent, or Firm—Joseph C. Gil; Richard E. L. Henderson

(57) ABSTRACT

Compound of the formula (I)

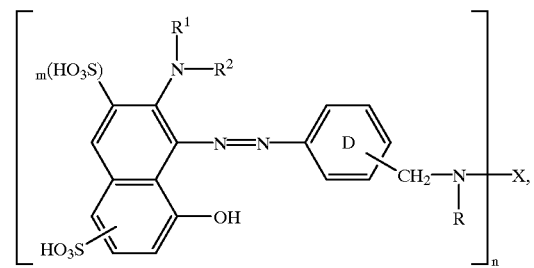

wherein

R is hydrogen or optionally substituted $C_1$–$C_6$-alkyl, $R^1$ is hydrogen or $C_1$–$C_6$-alkyl, $R^2$ is hydrogen, optionally substituted $C_1$–$C_6$-alkyl or optionally substituted phenyl, the ring D is optionally substituted by one or more identical or different substituents selected from the group consisting of $C_1$–$C_6$-alkyl, $C_1$–$C_6$-alkoxy, halogen, especially F, Cl and Br, and $SO_3H$, m is 0 or 1, n is 1, 2 or 3 and as a function of n X is a mono-, di- or trivalent acyl radical, pyrimidine or 1,3,5-triazine radical which is not fiber-reactive.

16 Claims, No Drawings

AZO DYES

The invention relates to new azo dyes, to a process for preparing them and to their use for dyeing and printing paper and other materials, especially as a dye in ink-jet inks.

The dyes of the invention have in the form of their free acids the formula (I)

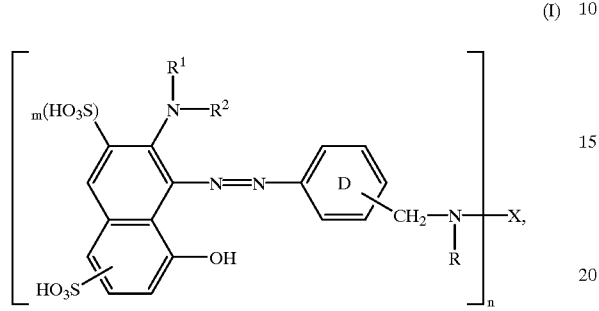

(I)

wherein

R is hydrogen or optionally substituted $C_1$–$C_6$-alkyl, $R^1$ is hydrogen or $C_1$–$C_6$-alkyl, $R^2$ is hydrogen, optionally substituted $C_1$–$C_6$-alkyl or optionally substituted phenyl, the ring D is optionally substituted by one or more identical or different substituents selected from the group consisting of $C_1$–$C_6$-alkyl, $C_1$–$C_6$-alkoxy, halogen, especially F, Cl and Br, and $SO_3H$, m is 0 or 1, n is 1, 2 or 3 and as a function of n X is a mono-, di- or trivalent acyl radical, pyrimidine or 1,3,5-triazine radical which is not fibre-reactive.

Exemplary substituents for optionally substituted alkyl radicals include for example: OH, $NR^3R^4$, where $R^3$ and $R^4$ independently of each other are hydrogen, $C_1$–$C_4$-alkyl, $C_2$–$C_4$-hydroxyalkyl.

Exemplary substituents for optionally substituted phenyl include for example: $C_1$–$C_6$-alkyl, $C_1$–$C_6$-alkoxy, COOH, $SO_3H$, F, Cl, Br.

Preferred dyes of the formula (I) are those wherein

R is hydrogen, $C_1$–$C_6$-alkyl or $C_2$–$C_4$-hydroxyalkyl, $R^1$ is hydrogen or $C_1$–$C_6$-alkyl, $R^2$ is hydrogen, $C_1$–$C_6$-alkyl, $C_2$–$C_4$-hydroxyalkyl, $C_2$–$C_4$-aminoalkyl, especially $NR^3R^4$-substituted $C_2$–$C_4$-alkyl, wherein $R^3$ and $R^4$ independently of each other represent hydrogen, $C_1$–$C_4$-alkyl and $C_2$–$C_4$-hydroxyalkyl or denote optionally $C_1$–$C_4$-alkyl-, $C_1$–$C_4$-alkoxy-, HOOC—, $HO_3S$—, F—, Cl— and/or Br-substituted phenyl, and the ring D is optionally substituted by one or more identical or different substituents selected from the group consisting of $C_1$–$C_4$-alkyl, $C_1$–$C_4$-alkoxy, F, Cl, Br and $SO_3H$.

In a particular embodiment when n=1 then X is optionally HOOC-substituted $C_2$–$C_6$-alkanoyl, optionally $C_1$–$C_4$-alkyl-, $C_1$–$C_4$-alkoxy-, $HO_3S$—, HOOC—, F—, Cl— and/or Br-substituted $C_6$–$C_{10}$-aroyl or a radical of the formulae (II), (IIIa) or (IIIb)

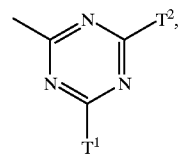

(II)

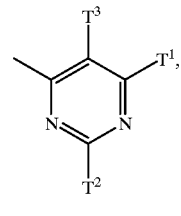

(IIIa)

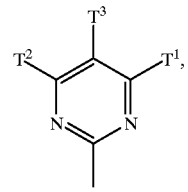

(IIIb)

wherein $T^1$ and $T^2$ independently of each other are $OR^5$, $NR^6R^7$ or $SR^8$, wherein $R^5$ and $R^8$ independently of each other are hydrogen, $C_1$–$C_6$-alkyl, sulpho-, carboxyl- and/or di-$C_1$–$C_3$-alkylamino-substituted $C_2$–$C_6$-alkyl or optionally $C_1$–$C_4$-alkyl-, $C_1$–$C_4$-alkoxy-, sulpho-, F—, Br— and/or Cl-substituted phenyl, $R^6$ is hydrogen, $C_1$–$C_6$-alkyl or $C_2$–$C_6$-alkyl optionally substituted by sulphur, hydroxyl, $C_1$–$C_3$-alkoxy, amino or mono- or disubstituted $C_1$–$C_3$-alkylamino, $R^7$ has the meanings of $R^6$ independently of $R^6$ or is optionally $C_1$–$C_4$-alkyl-, $C_1$–$C_4$-alkoxy-, carboxyl-, sulpho-, F—, Cl—and/or Br-substituted phenyl or naphthyl, or $R^6$ and $R^7$ combine with the nitrogen atom to which they are attached to form a morpholine radical or an optionally $C_1$–$C_4$-alkyl-, $C_2$–$C_4$-hydroxyalkyl- or $C_2$–$C_4$-aminoalkyl-substituted piperazine radical, and $T^3$ is hydrogen, F, Cl, CN, $CCl_3$, $CCl_2F$ or COOH.

In a further particular embodiment when n=2 X is —CO—, —CO—$(CH_2)_{1-4}$—CO—, —$COC_2H_2$—CO—, optionally $H_3C$—, $H_3CO$—, F—, Cl—, Br— and/or HOOC-substituted $C_6$–$C_{10}$-diaroyl or a radical of the formulae (IVa), (IVb) or (V)

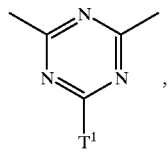

(IVa)

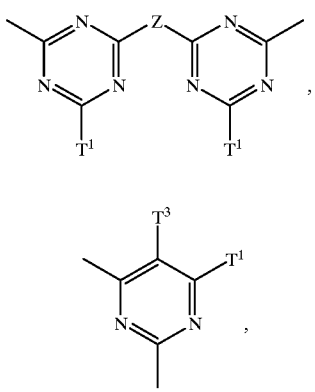

(IVb)

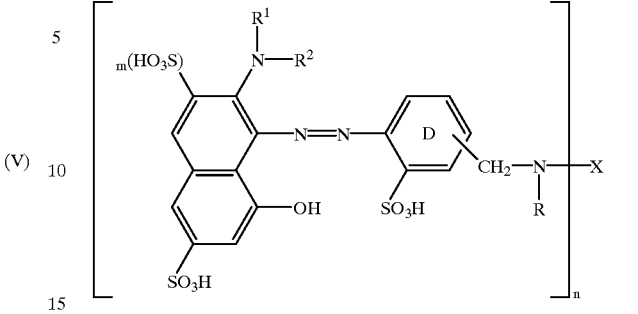

(VIII)

wherein

R, R¹, R², D, X and m are each as defined above,
n is 1 or 2.

Particular preference in this context is given to dyes of the formula (VIII) wherein m=0.

Very particular preference is given to dyes of the formula (VIII) wherein R, R¹ and R² are each as defined above, m=0, the ring D does not bear any further substituents, and X is benzoyl or a radical of the formula (II) when n=1 and CO, $COC_2H_4CO$, $COC_2H_2CO$,

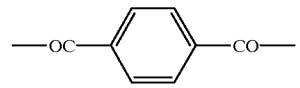

or a radical of the formula (IVa) or (IVb) when n=2.

In a preferred embodiment, the substituents of the compound of the formula (I) and its subformulae have the following meanings:

$R^1$ and $R^2$ independently of each other are preferably hydrogen, $CH_3$, $C_2H_5$, $C_3H_7$, $C_2H_4OH$, $C_2H_4SO_3H$, $C_3H_6OH$, $C_3H_6SO_3H$, $C_2H_4COOH$, $C_3H_6COOH$, $C_6H_5$, $C_6H_4SO_3H$, $C_6H_4COOH$ or $C_2H_4N(CH_3)_2$.

R is preferably hydrogen, $CH_3$, $C_2H_5$, $C_2H_4OH$.

$R^3$ and $R^4$ independently of each other are preferably hydrogen, $CH_3$, $C_2H_4OH$.

$R^5$ is preferably derived from the following $HOR^5$ compounds: ethylene glycol or isethionic acid (2-hydroxyethanesulphonic acid), water.

$R^6$ is preferably hydrogen, $CH_3$, $C_2H_5$, $C_3H_7$, $C_2H_4OH$, $C_2H_4OCH_3$ or $C_3H_6OH$.

$R^7$ is preferably hydrogen, $C_2H_4OH$, $C_3H_6OH$, $C_2H_4SO_3H$, $C_2H_4COOH$, $C_3H_6SO_3H$, $C_3H_6COOH$, $C_6H_5$, $C_6H_4SO_3H$, $C_6H_4COOH$ or $R^6$ and $R^7$ combine with the nitrogen atom to which they are bonded to preferably denote a radical of the formula

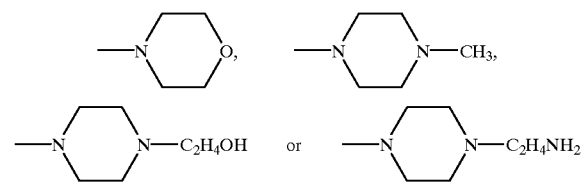

$R^8$ is preferably derived from the following thiols $HSR^8$: 2-mercaptoethanol or 3-mercapto-1-propanesulphonic acid.

(V)

wherein $T^1$ and $T^3$ are each as defined above and

Z is a radical of the formula

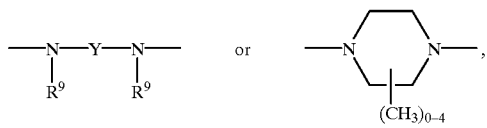

Y is $C_2$–$C_6$-alkylene or optionally carboxyl- or sulpho-substituted arylene, and $R^9$ is hydrogen, $C_1$–$C_6$-alkyl or $C_2$–$C_4$-hydroxyalkyl.

In a likewise particular embodiment when n=3 X is a radical of the formula (VI) or (VII)

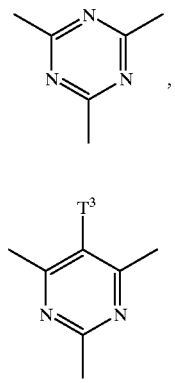

(VI)

(VIII)

wherein $T^3$ is as defined above.

Particular preference is given to compounds of the formula (I) which conform to the formula (VIII)

$R^9$ is preferably hydrogen, $CH_3$, $C_2H_4OH$.

$T^1$ and $T^2$ independently of each other are preferably derived respectively from the following amines $T^1H$ and $T^2H$:

2-aminoethanol, 2-methylaminoethanol, 1-amino-2-propanol, 2-amino-1-propanol, diethanolamine, taurine, N-methyltaurine, glycine, 3-aminopropanoic acid, 3-dimethylamino-1-propylamine, N-2-hydroxyethyl-piperazine, N-2-aminoethylpiperazine, morpholine, aniline, orthanilic acid, methanilic acid, sulphanilic acid, anthranilic acid, 3-aminobenzoic acid, 4-aminobenzoic acid, ammonia.

Z is preferably:

m-phenylenediamine, p-phenylenediamine, 2,4-diaminobenzenesulphonic acid, 2,5-diaminobenzenesulphonic acid, piperazine, 2,5-dimethylpiperazine.

Very particular preference is likewise given to compounds of the formula (I) which conform to the formula (IX)

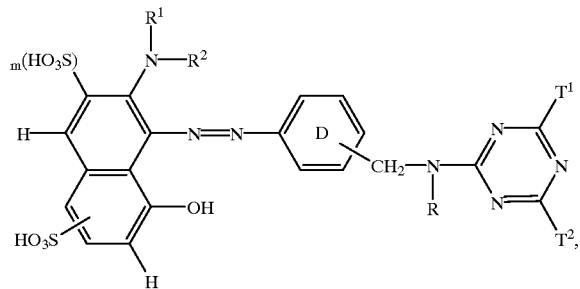

(IX)

wherein the substituents are each as defined above.

Very particular preference is given to compounds of the formula (X)

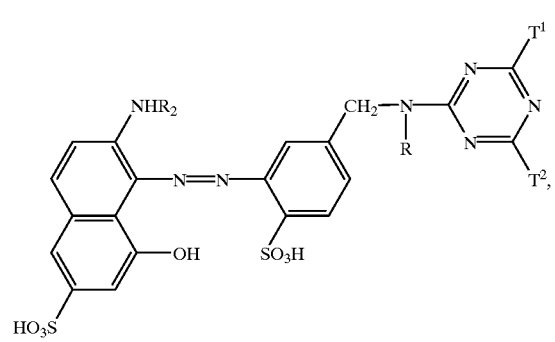

(X)

wherein

R is hydrogen, $CH_3$ or $C_2H_5$, $R^2$ is hydrogen, $CH_3$, $C_2H_5$, $C_3H_7$, $C_4H_9$ or $C_6H_5$, and $T^1$ and $T^2$ are each as defined above and preferably represent OH, $NH_2$, $NH_2C_2H_4OH$, $N(C_2H_4OH)_2$, $NHC_2H_4SO_3H$, $CH_2NC_2H_4SO_3H$.

The dyes of the formula (I) are preferably used in the form of their lithium, sodium, potassium or ammonium salts. Useful ammonium salts are in particular ammonium salts in which 1 to 4 hydrogen atoms are replaced by identical or different $C_1$–$C_6$-alkyl radicals or hydroxyl- or $C_1$–$C_3$-alkoxy-substituted $C_2$–$C_6$-alkyl radicals. Particular preference is given to alkanolamine ammonium salts such as methyldiethanolammonium, dimethylethanolammonium or triethanolammonium and quaternary ammonium ions such as tetramethylammonium and tetraethylammonium.

The invention further provides a process for preparing the compounds of the formula (I) according to the invention, which is characterized in that compounds of the formula (XI)

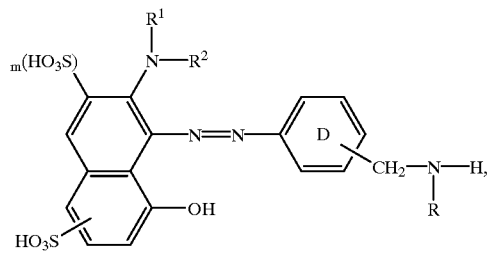

(XI)

wherein

R, $R^1$, $R^2$, D and m are each as defined above, are reacted with compounds of the formula $X(B)_n$, where X is as defined above as a function of n, n is 1, 2 or 3, and B is a detachable Cl or F radical.

The preferred compounds of the formula $X(B)_n$ are carbonyl halides, methyl carboxylates and 2,4,6-trifluoro- or 2,4,6-trichloropyrimidines or -1,3,5-triazines with any fluorine or chlorine atoms still present in these reaction products in the 4- and/or 6-position being replaced by HN-, HO- or HS-containing nucleophiles.

Preferred acylating agents of the formula $X(B)_n$ are carbonyl chlorides, for example acetyl chloride, propionyl chloride, benzoyl chloride, terephthaloyl chloride, succinoyl chloride, fumaroyl chloride, phosgene and carboxylic anhydride, for example acetic anhydride.

Preferred pyrimidines of the formula $X(B)_n$ are 2,4,6-trifluoropyrimidine, 5-chloro-2,4,6-trifluoropyrimidine, 5-cyano-2,4,6-trifluoropyrimidine, 2,4,5,6-tetrachloropyrimidine.

Preferred triazines of the formula $X(B)_n$ are 2,4,6-trifluoro- and 2,4,6-trichloro-1,3,5-triazine.

The compounds of the formula (XI) are known: (CAS-RN 77850-13-6) or can be obtained in a similar manner. The conditions for the reaction of compounds of the formula (XI) with acylating agents or with 2,4,6-trifluoro- or 2,4,6-trichloropyrimidine or -1,3,5-triazine are likewise known (for example DE-A-29 35 681, EP-65 479).

Also known are the conditions for reacting any fluorine or chlorine atoms still present in the 4- and/or 6-position of these pyrimidine- or triazine-containing reaction products with HN-, HO- or HS-containing nucleophiles (EP-755 984, WO 96/24 635, EP-682 088).

The invention further provides a process for dyeing cellulosic materials with the dyes of the formula (I).

The compounds of the formula (I) according to the invention can be used as solid or liquid dye preparations. They are preferably used in the form of aqueous preparations, especially in the form of solutions. These aqueous dye preparations generally include one or more dyes of the formula (I), optionally suitable organic solvents, including hydrotropic compounds, and also further auxiliaries and/or stabilizers. It is advantageous to prepare the aqueous dye solutions in the course of the dye synthesis itself, without intermediate isolation of the dye.

The use-form of the aqueous dye preparations is particularly preferred for the dyeing or printing of paper. A stable, aqueously concentrated dyeing preparation can be prepared in a general manner, by dissolving the dye in water with or without addition of one or more auxiliaries, for example a hydrotropic compound or a stabilizer.

The aqueous dye preparations generally contain about 0.5 to 20% by weight of one or more dyes of the formula (I) and 80 to 99.5% by weight of water and/or solvents with or without further customary ingredients.

Preferred organic solvents are alcohols and their ethers or esters, carboxamides, ureas, sulphoxides and sulphones, especially those having molecular weights <200. Examples of particularly suitable solvents are: methanol, ethanol, propanol; ethylene glycol, propylene glycol, diethylene glycol, thiodiethylene glycol and dipropylene glycol; butanediol; β-hydroxypropionitrile, pentamethylene glycol, ethylene glycol monoethyl and propyl ether, ethylene diglycol monoethyl ether, triethylene glycol monobutyl ether, butylpolyglycol, formamide, triethylene glycol, 1,5-pentanediol, 1,3,6-hexanetriol, 2-hydroxyethyl acetate, 2-(2'-hydroxy)ethyl acetate, glycerol, glycol acetate, 1,2-dihydroxypropane, 1-methoxy-2-propanol, 2-methoxy-1-propanol, N,N-dimethylformamide, pyrrolidone, N-methylcaprolactam, ε-caprolactam, butyrolactone, urea, tetramethylurea, 1,3-dimethyl-2-imidazolidinone, N,N'-dimethylolpropyleneurea, dimethyl sulphoxide, dimethyl sulphone, sulpholane, isopropanol, polyethylene glycol.

Useful further additives customary for aqueous dye preparations, especially for waterborne printing inks, include those ionic or nonionic substances with which the viscosity and/or surface tension can be set to within the ranges required for use, for example anionic, cationic or neutral surfactants such as dispersants and viscosity regulators. The function of viscosity regulators can be assumed by the organic solvents, for example.

Preference is given to aqueous dye preparations, especially dye solutions, comprising 0.5 to 20% by weight, especially 1 to 15% by weight, of one or more dyes of which at least one corresponds to the compound of claim 1 or to a salt thereof, 50 to 99.5% by weight, especially 85 to 99% by weight, of water, 0 to 30% by weight, especially 0 to 20% by weight, of one or more organic solvents, 0 to 30% by weight, especially 0 to 10% by weight, of additives to influence the viscosity and/or the surface tension, the ingredients mentioned preferably adding up to 100% by weight.

The aqueous dye preparations may be produced by dissolving the dye salts in water or from the condensation solutions, which are optionally subjected to an isomer exchange and/or a desalting operation for example through pressure permeation, and/or by addition of one or more of the abovementioned organic solvents optionally at elevated temperatures (30 to 100° C., especially 30 to 50° C.) and with addition of inorganic and organic bases; if necessary, customary ionic or nonionic additives can be used in addition, for example those with which the viscosity can be lowered and/or the surface tension raised.

Instead of the salts of (I), it is also possible to use the corresponding free acids in combination with at least equimolar amounts of the corresponding organic or inorganic bases.

The aqueous dye preparations of the invention are also used for preparing waterborne printing inks which may be used in particular also as recording fluids by the ink-jet method.

The invention accordingly further provides printing inks comprising at least one dye (I) and their use as recording fluid for ink-jet recording systems to produce red prints.

In the ink-jet method of the process of the invention, ink droplets are sprayed onto the subject. The fine ink droplets can be generated by different methods. Preferably, they are generated according to the generally known thermal-jet, bubble-jet, piezo-jet or valve ink-jet processes.

The use of the dyes of the invention in the form of their aqueous preparations, especially of their waterborne printing inks as recording fluid for ink-jet recording systems, provides for the following advantages: The physical properties, such as viscosity, surface tension and the like, are within the suitable ranges; the recording fluid does not cause blockages in fine discharge openings of ink-jet recording devices; it provides images of high density; in storage, the recording fluid does not change its physical properties and does not sediment solid constituents; the recording fluid is useful for recording on various recording media without restrictions with regard to the nature of the recording media; finally, the recording fluid is quick to fix and provides images possessing excellent water resistance, lightfastness, rub-off resistance and resolution.

The preparation examples hereinbelow are intended to elucidate the present invention without, however, restricting it thereto. In the examples, parts are always by weight, unless otherwise stated.

The dyeings and prints obtained with the dyes of the invention, especially the prints obtained by the ink-jet method on paper, possess outstanding brilliance.

EXAMPLES

Example 1

48.0 g of the compound of the formula

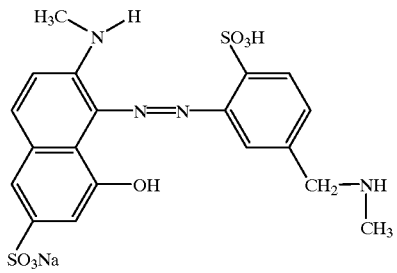

are dissolved in 1000 ml of water at neutral pH with the aid of sodium carbonate. After addition of 19 g of 2,4,6-trichloro-1,3,5-triazine, the batch is stirred at 0–5° C. while the pH is maintained at 7.5 by addition of sodium carbonate solution. After the condensation has ended, 13 g of taurine are added; the batch is heated to 40° C. while the pH is maintained at 7.5–8 by addition of sodium carbonate solution. After the second condensation has ended, 21 g of diethanolamine are added; the batch is heated to the boil until the third condensation has ended.

The resulting solution of the dye of the formula

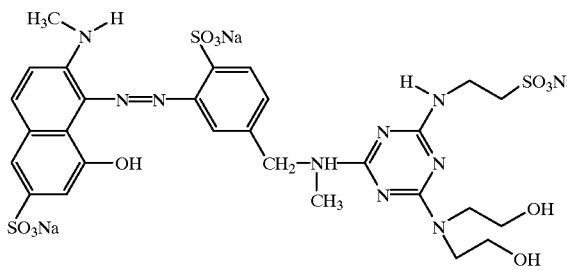

is substantially desalted in a pressure permeation apparatus and concentrated at the end until the $E_1^1$ value of the absorption maximum is 40 ($\lambda_{max}$=539 nm).

$E_1^1$ standardized extinction of a 1% strength solution (water) at a path length of 1 cm.

Example 2

10 g concentrated solution of Example 1 are stirred up with 70 g of water and 20 of 1,5-pentanediol. This produces an ink which, when printed up on a commercially available inkjet printer, provides red brilliant lightfast prints on commercially available papers.

The table hereinbelow recites further dyes prepared using the reported compounds for the second and third condensations with 2,4,6-trichloro-1,3,5-triazine. When 3-mercaptopropanesulphonic acid and 2-mercaptoethanol are used, the amount of sodium carbonate required for deprotonating the SH group is also added.

| Example | 2nd condensation | 3rd condensation |
|---|---|---|
| 3 | N-methyltaurine | ethanolamine |
| 4 | 3-mercaptopropane-sulphonic acid | sodium hydroxide |
| 5 | anthranilic acid | sodium hydroxide |
| 6 | metanilic acid | morpholine |
| 7 | 3-mercaptopropane-sulphonic acid | 3-mercaptopropane-sulphonic acid |
| 8 | anthranilic acid | diethanolamine |
| 9 | 3-mercaptopropane-sulphonic acid | diethanolamine |

The resulting solutions contain the dyes of the formulae

Example 3

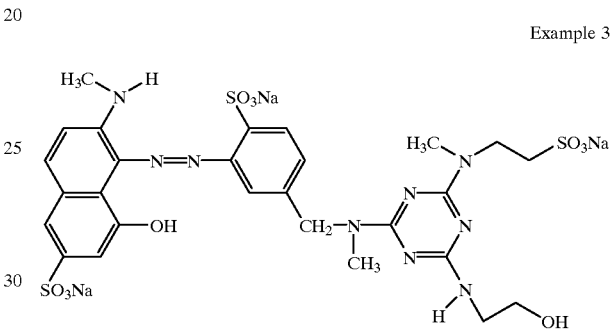

Example 4

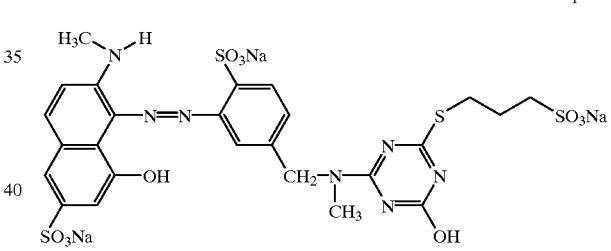

Example 5

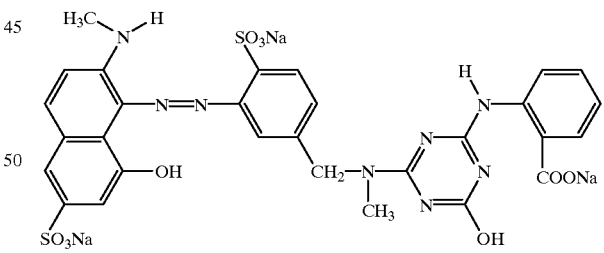

Example 6

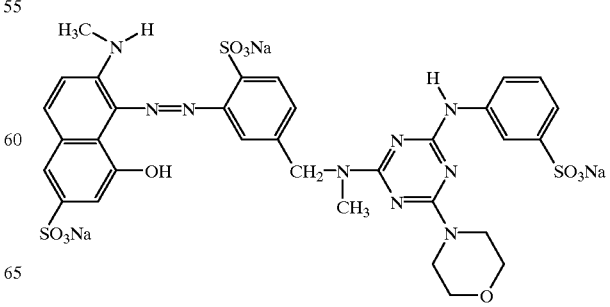

Example 7

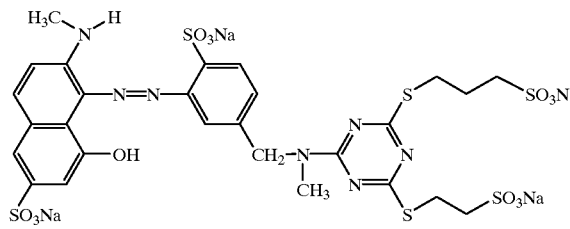

Example 8

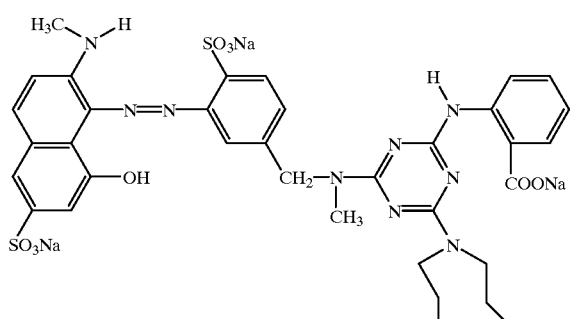

Example 9

Replacing the 3-mercaptopropanesulphonic acid used in Example 7 with equimolar amounts of ethanolamine, diethanolamine, N-methylethanolamine, taurine, N-methyltaurine, morpholine, N-2-hydroxyethylpiperazine, 2-mercaptoethanol, ammonia or sodium hydroxide solution likewise provides solutions of a red dye.

Example 10

Replacing the taurine used in Example 1 with a further 48 g of the azo compound used in the first condensation provides a solution of the dye of the formula

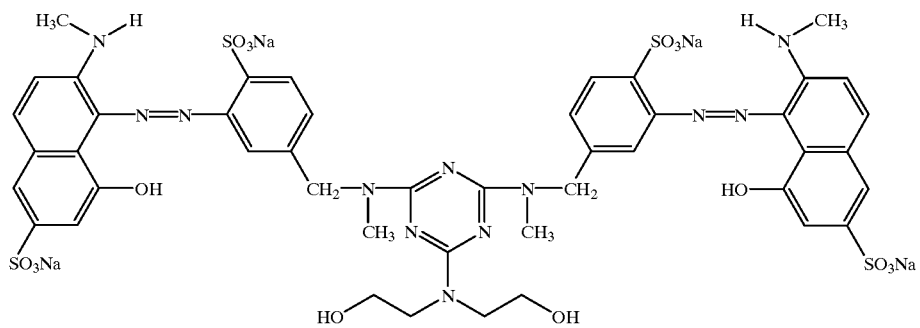

Example 11

Replacing the diethanolamine used in Example 10 with an equimolar amount of sodium hydroxide provides a solution of the dye of the formula

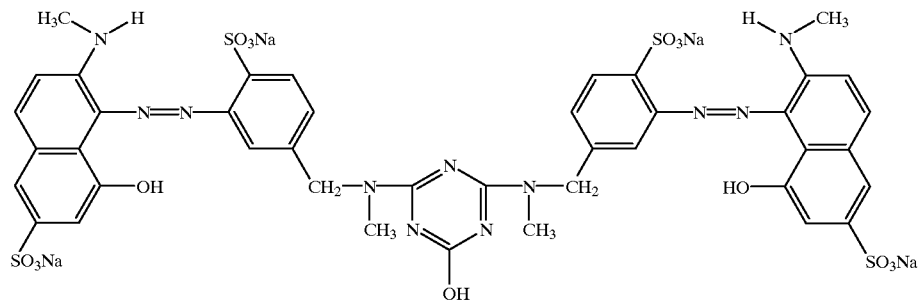

The use of ethanolamine, taurine, N-methyltaurine, morpholine, N-2-hydroxyethylpiperazine, 2-mercaptoethanol, 3-mercapto-propanesulphonic acid or ammonia instead of sodium hydroxide provides the corresponding dyes whose use in ink-jet inks likewise provides brilliant lightfast red prints.

Example 12

48 g of the azo compound of Example 1 are dissolved in 1000 ml of water at a neutral pH with the aid of lithium carbonate. After addition of 10.1 g of terephthaloyl chloride, the batch is stirred at 20 to 25° C. while the pH is maintained at 7.5 to 8 by addition of lithium hyroxide solution to obtain a solution of the dye of the formula

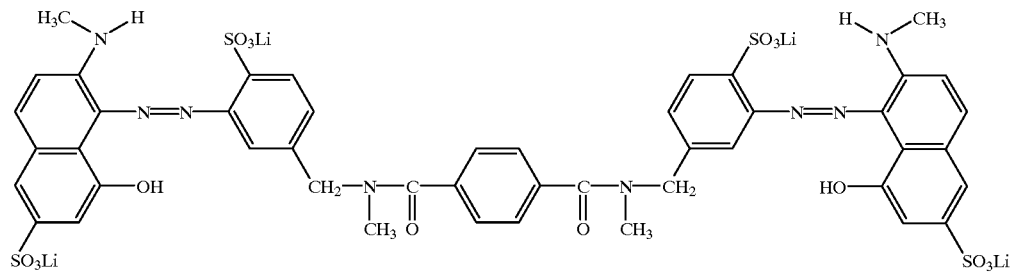

Example 13

Replacing the taurine used in Example 1 with 5.2 g of 1,4-diaminobenzene and the diethanolamine with an equimolar amount of taurine provides the red dye of the formula

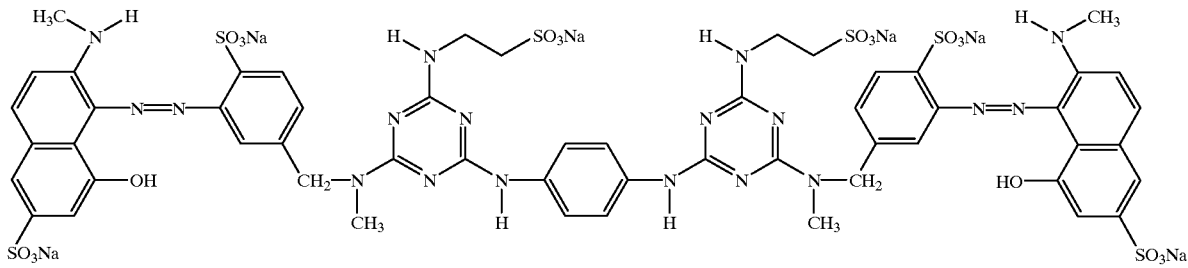

The table hereinbelow recites further dyes prepared using the reported compounds for the second and third condensations with 2,4,6-trichloro-1,3,5-triazine.

| Example | 2nd condensation | 3rd condensation |
|---|---|---|
| 14 | 1,3-diaminobenzene | N-methyltaurine |
| 15 | 2,5-dimethylpiperazine | sodium hydroxide |
| 16 | 2,5-diaminobenzenesulphonic acid | diethanolamine |
| 17 | 4,4'-diaminostilbene-2,2'-disulphonic acid | ethanolamine |

What is claimed is:

1. A compound of the formula (I)

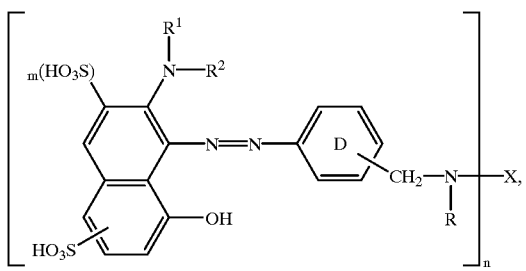

(I)

wherein

R is hydrogen, $C_1$–$C_6$-alkyl, or substituted $C_1$–$C_6$-alkyl, $R^1$ is hydrogen or $C_1$–$C_6$-alkyl, $R^2$ is hydrogen, $C_1$–$C_6$-alkyl, substituted $C_1$–$C_6$-alkyl, phenyl, or substituted phenyl, ring D is not further substituted or is further substituted with one or more identical or different substituents selected from the group consisting of $C_1$–$C_6$-alkyl, $C_1$–$C_6$-alkoxy, halogen, and $SO_3H$, m is 0 or 1, n is 1, 2, or 3, and X is a monovalent, divalent, or trivalent acyl radical, pyrimidine radical, or 1,3,5-triazine radical that is not fiber-reactive.

2. A compound according to claim 1 having the formula (VIII)

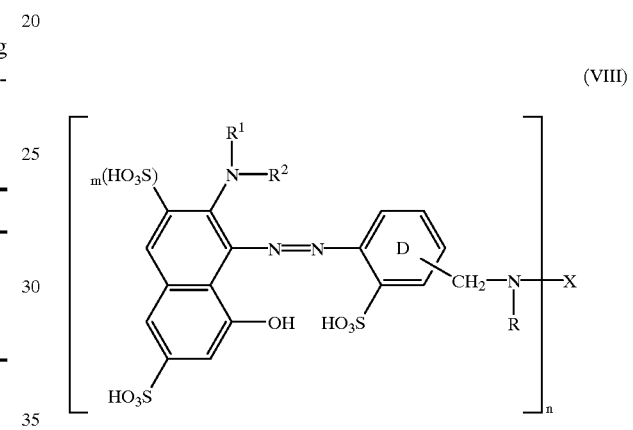

(VIII)

wherein

R is hydrogen, $C_1$–$C_6$-alkyl, or substituted $C_1$–$C_6$-alkyl, $R^1$ is hydrogen or $C_1$–$C_6$-alkyl, $R^2$ is hydrogen, $C_1$–$C_6$-alkyl, substituted $C_1$–$C_6$-alkyl, phenyl, or substituted phenyl, ring D is not further substituted or is further substituted with one or more identical or different substituents selected from the group consisting of $C_1$–$C_6$-alkyl, $C_1$–$C_6$-alkoxy, halogen, and $SO_3H$, m is 0 or 1, n is 1 or 2, and X is a monovalent or divalent acyl radical, pyrimidine radical, or 1,3,5-triazine radical that is not fiber-reactive.

3. A compound according to claim 1 wherein

R is hydrogen, $C_1$–$C_6$-alkyl, or $C_2$–$C_4$-hydroxyalkyl, $R^1$ is hydrogen or $C_1$–$C_6$-alkyl, $R^2$ is hydrogen, $C_1$–$C_6$-alkyl, $C_2$–$C_4$-hydroxyalkyl, or $C_2$–$C_4$-aminoalkyl, and ring D is not further substituted or is further substituted with one or more identical or different substituents selected from the group consisting of $C_1$–$C_4$-alkyl, $C_1$–$C_4$-alkoxy, F, Cl, and Br.

4. A compound according to claim 3 wherein $R^2$ is $NR^3R^4$-substituted $C_2$–$C_4$-alkyl, wherein $R^3$ and $R^4$ independently represent hydrogen, $C_1$–$C_4$-alkyl, $C_2$–$C_4$-hydroxyalkyl, phenyl, or phenyl substituted with $C_1$–$C_4$-alkyl, $C_1$–$C_4$-alkoxy, HOOC, $HO_3S$, F, Cl, Br, or a combination thereof.

5. A compound according to claim 1 wherein n is 1 and

X is $C_2$–$C_6$-alkanoyl, HOOC-substituted $C_2$–$C_6$-alkanoyl, aroyl, aroyl substituted with $C_1$–$C_4$-alkyl, $C_1$–$C_4$-alkoxy, $HO_3S$, HOOC, F, Cl, Br, or a combination thereof, or a radical of the formulas (II), (IIa), or (IIIb)

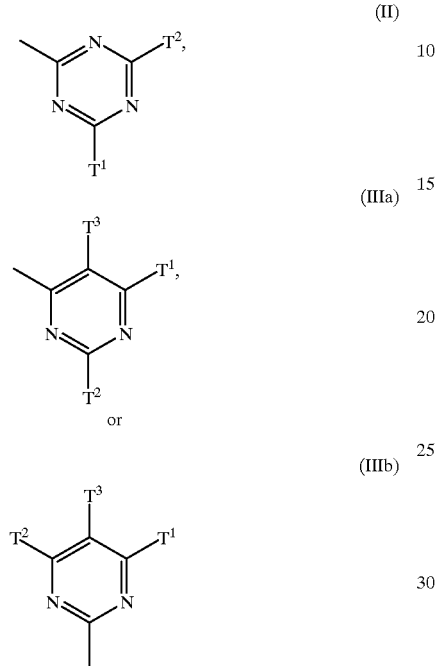

wherein $T^1$ and $T^2$ independently are $OR^5$, $NR^6R^7$, or $SR^8$, wherein $R^5$ and $R^8$ independently are hydrogen, $C_1$–$C_6$-alkyl, $C_1$–$C_6$-alkyl substituted with sulpho, carboxyl, di($C_1$–$C_3$-alkyl)amino, or a combination thereof, phenyl, or phenyl substituted with $C_1$–$C_4$-alkyl, $C_1$–$C_4$-alkoxy, sulpho, F, Br, Cl, or a combination thereof, $R^6$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkylamino, or disubstituted $C_1$–$C_3$-alkylamino, $R^7$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkyl-amino, disubstituted $C_1$–$C_3$-alkylamino, phenyl, phenyl substituted with $C_1$–$C_4$-alkyl, $C_1$–$C_4$-alkoxy, carboxyl, sulpho, F, Cl, Br, or a combination thereof, naphthyl, or naphthyl substituted with $C_1$–$C_4$-alkyl, $C_1$–$C_4$-alkoxy, carboxyl, sulpho, F, Cl, Br, or a combination thereof, or $R^6$ and $R^7$ together combine with the nitrogen atom to which they are attached to form a morpholine radical, a piperazine radical, or a piperazine radical substituted with $C_1$–$C_4$-alkyl, $C_2$–$C_4$-hydroxy-alkyl, or $C_2$–$C_4$-aminoalkyl, and $T^3$ is hydrogen, F, Cl, CN, $CCl_3$, $CCl_2F$, or COOH.

6. A compound according to claim 1 wherein n is 2 and

X is —CO—, —CO—$(CH_2)_{1-4}$—CO—, —$COC_2H_2$—CO—, $C_6$–$C_{10}$-diaroyl, $C_6$–$C_{10}$-diaroyl substituted with $CH_3$, $CH_3O$, F, Cl, Br, HOOC, or a combination thereof, or a radical of the formulas (IVa), (IVb), or (V)

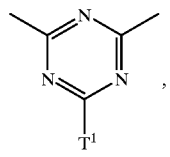

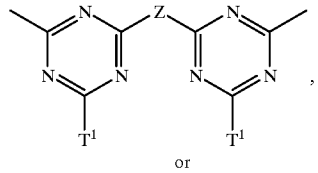

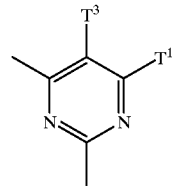

wherein $T^1$ is $OR^5$, $NR^6R^7$, or $SR^8$, wherein $R^5$ and $R^8$ independently are hydrogen, $C_1$–$C_6$-alkyl, $C_1$–$C_6$-alkyl substituted with sulpho, carboxyl, di($C_1$–$C_3$-alkyl)amino, or a combination thereof, phenyl, or phenyl substituted with $C_1$–$C_4$-alkyl, $C_1$–$C_4$-alkoxy, sulpho, F, Br, Cl or a combination thereof, $R^6$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkyl-amino, or disubstituted $C_1$–$C_3$-alkylamino, $R^7$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkyl-amino, disubstituted $C_1$–$C_3$-alkylamino, phenyl, phenyl substituted with $C_1$–$C_4$-alkyl, $C_1$–$C_4$-alkoxy, carboxyl, sulpho, F, Cl, Br, or a combination thereof, naphthyl, or naphthyl substituted with $C_1$–$C_4$-alkyl, $C_1$–$C_4$-alkoxy, carboxyl, sulpho, F, Cl, Br, or a combination thereof, or $R^6$ and $R^7$ together combine with the nitrogen atom to which they are attached to form a morpholine radical, a piperazine radical, or a piperazine radical substituted with $C_1$–$C_4$-alkyl, $C_2$–$C_4$-hydroxy-alkyl, or $C_2$–$C_4$-aminoalkyl, and $T^3$ is hydrogen, F, Cl, CN, $CCl_3$, $CCl_2F$, or COOH, and Z is a radical of the formula

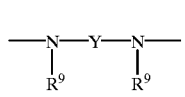 or 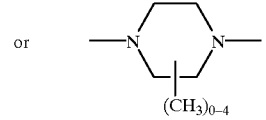

wherein

Y is $C_2$–$C_6$-alkylene, arylene, or carboxyl- or sulphato-substituted arylene, and $R^9$ is hydrogen, $C_1$–$C_6$-alkyl, or $C_2$–$C_4$-hydroxyalkyl.

7. A compound according to claim 1 wherein n is 3 and

X is a radical of the formula (VI) or (VII)

(VI)

[triazine structure]

or (VIII)

[pyrimidine structure with $T^3$]

wherein $T^3$ is hydrogen, F, Cl, CN, $CCl_3$, $CCl_2F$, or COOH.

8. A compound according to claim 6 wherein $R^1$ and $R^2$ independently are hydrogen, $CH_3$, $C_2H_5$, $C_3H_7$, $C_2H_4OH$, $C_2H_4SO_3H$, $C_3H_6OH$, $C_3H_6SO_3H$, $C_2H_4COOH$, $C_3H_6COOH$, $C_6H_5$, $C_6H_4SO_3H$, $C_6H_4COOH$, or $C_2H_4N(CH_3)_2$, R is hydrogen, $CH_3$, $C_2H_5$, or $C_2H_4OH$, $R^3$ and $R^4$ independently are hydrogen, $CH_3$, or $C_2H_4OH$, $R^5$ is derived from a $HOR^5$ compound selected from the group consisting of ethylene glycol and 2-hydroxyethanesulphonic acid, $R^6$ is hydrogen, $CH_3$, $C_2H_5$, $C_3H_7$, $C_2H_4OH$, $C_2H_4OCH_3$, or $C_3H_6OH$, $R^7$ is hydrogen, $C_2H_4OH$, $C_3H_6OH$, $C_2H_4SO_3H$, $C_2H_4COOH$, $C_3H_6SO_3H$, $C_3H_6COOH$, $C_6H_5$, $C_6H_4SO_3H$, or $C_6H_4COOH$, or $R^6$ and $R^7$ combine with the nitrogen atom to which they are bonded to form a radical of the formula

[morpholine], [N-methylpiperazine],

[N-hydroxyethylpiperazine], or [N-aminoethylpiperazine]

$R^8$ is derived from a thiol $HSR^8$ selected from the group consisting of 2-mercaptoethanol and 3-mercapto-1-propanesulphonic acid, and $R^9$ is hydrogen, $CH_3$, or $C_2H_4OH$.

9. A compound according to claim 1 having the formula (IX)

(IX)

[naphthalene-azo-benzene-triazine structure with substituents $R^1$, $R^2$, $(HO_3S)_m$, $HO_3S$, OH, D, $CH_2$–N(R), $T^1$, $T^2$]

wherein

R is hydrogen, $C_1$–$C_6$-alkyl, or substituted $C_1$–$C_6$-alkyl, $R^1$ is hydrogen or $C_1$–$C_6$-alkyl, $R^2$ is hydrogen, $C_1$–$C_6$-alkyl, substituted $C_1$–$C_6$-alkyl, phenyl, or substituted phenyl, ring D is not further substituted or is further substituted with one or more identical or different substituents selected from the group consisting of $C_1$–$C_6$-alkyl, $C_1$–$C_6$-alkoxy, halogen, and $SO_3H$, m is 0 or 1, and $T^1$ and $T^2$ independently are $OR^5$, $NR^6R^7$, or $SR^8$, wherein $R^5$ and $R^8$ independently are hydrogen, $C_1$–$C_6$-alkyl, $C_1$–$C_6$-alkyl substituted with sulpho, carboxyl, di($C_1$–$C_3$-alkyl)amino, or a combination thereof, phenyl, or phenyl substituted with $C_1$–$C_4$-alkyl, $C_1$–$C_4$-alkoxy, sulpho, F, Br, Cl, or a combination thereof, $R^6$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkylamino, or disubstituted $C_1$–$C_3$-alkylamino, and $R^7$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkylamino, disubstituted $C_1$–$C_3$-alkylamino, phenyl, phenyl substituted with $C_1$–$C_4$-alkyl, $C_1$–$C_4$-alkoxy, carboxyl, sulpho, F, Cl, Br, or a combination thereof, naphthyl, or naphthyl substituted with $C_1$–$C_4$-alkyl, $C_1$–$C_4$-alkoxy, carboxyl, sulpho, F, Cl, Br, or a combination thereof, or $R^6$ and $R^7$ together combine with the nitrogen atom to which they are attached to form a morpholine radical, a piperazine radical, or a piperazine radical substituted with $C_1$–$C_4$-alkyl, $C_2$–$C_4$-hydroxyalkyl, or $C_2$–$C_4$-aminoalkyl.

10. A compound according to claim 5 having the formula (X)

(X)

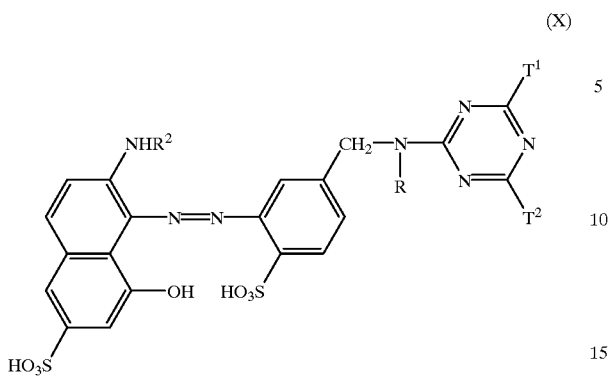

wherein

R is hydrogen, $CH_3$, or $C_2H_5$, $R^2$ is hydrogen, $CH_3$, $C_2H_5$, $C_3H_7$, $C_4H_9$, or $C_6H_5$, and $T^1$ and $T^2$ independently are $OR^5$, $NR^6R^7$, or $SR^8$, wherein $R^5$ and $R^8$ independently are hydrogen, $C_1$–$C_6$-alkyl, $C_1$–$C_6$-alkyl substituted with sulpho, carboxyl, di($C_1$–$C_3$-alkyl)amino, or a combination thereof, phenyl, or phenyl substituted with $C_1$-$C_4$-alkyl, $C_1$-$C_4$-alkoxy, sulpho, F, Br, Cl, or a combination thereof, $R^6$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkylamino, or disubstituted $C_1$–$C_3$-alkylamino, $R^7$ is hydrogen, $C_1$–$C_6$-alkyl, $C_2$–$C_6$-alkyl substituted with sulphur, hydroxyl, $C_1$–$C_3$-alkoxy, amino, monosubstituted $C_1$–$C_3$-alkylamino, disubstituted $C_1$–$C_3$-alkylamino, phenyl, phenyl substituted with $C_1$–$C_4$-alkyl, $C_1$–$C_4$-alkoxy, carboxyl, sulpho, F, Cl, Br, or a combination thereof, naphthyl, or naphthyl substituted with $C_1$–$C_4$-alkyl, $C_1$–$C_4$-alkoxy, carboxyl, sulpho, F, Cl, Br, or a combination thereof, or $R^6$ and $R^7$ together combine with the nitrogen atom to which they are attached to form a morpholine radical, a piperazine radical, or a piperazine radical substituted with $C_1$–$C_4$-alkyl, $C_2$–$C_4$-hydroxyalkyl, or $C_2$–$C_4$-aminoalkyl.

11. A compound according to claim 10 wherein $T^1$ and $T^2$ independently represent hydrogen, $CH_3$, or $C_2H_4OH$.

12. A process for preparing a compound according to claim 1 comprising reacting (1) a compound of the formula (XI)

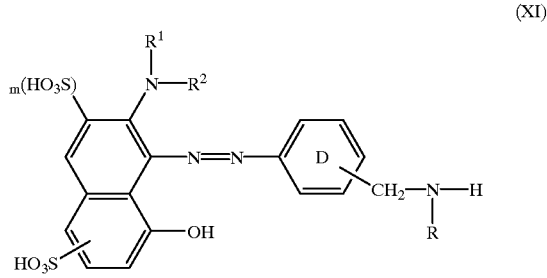

wherein

R is hydrogen, $C_1$–$C_6$-alkyl, or substituted $C_1$–$C_6$-alkyl, $R^1$ is hydrogen or $C_1$–$C_6$-alkyl, $R^2$ is hydrogen, $C_1$–$C_6$-alkyl, substituted $C_1$–$C_6$-alkyl, phenyl, or substituted phenyl, ring D is not further substituted or is further substituted with one or more identical or different substituents selected from the group consisting of $C_1$–$C_6$-alkyl, $C_1$–$C_6$-alkoxy, halogen, and $SO_3H$, and m is 0 or 1, with (2) a compound of the formula
$X(B)_n$,
wherein X is a monovalent, divalent, or trivalent acyl radical, pyrimidine radical, or 1,3,5-triazine radical that is not fiber-reactive, n is 1,2 or 3, and B is a detachable Cl or F radical.

13. An aqueous dye preparation comprising (1) 0.5 to 20% by weight of one or more dyes wherein at least one such dye corresponds to a compound of claim 1 or a salt thereof, (2) 50 to 99.5% by weight of water, (3) 0 to 30% by weight of one or more organic solvents, and (4) 0 to 30% by weight of additives that influence viscosity and/or surface tension.

14. A printing ink comprising at least one dye corresponding to a compound according to claim 1.

15. A method for dyeing or printing substrates containing hydroxyl groups or amido groups or both hydroxyl and amido groups comprising applying a compound according to claim 1 to the substrate.

16. A method for printing paper comprising applying a compound according to claim 1 to paper by the inkjet method.

* * * * *